United States Patent
Glidden

(10) Patent No.: US 11,649,259 B2
(45) Date of Patent: May 16, 2023

(54) POLYMORPHIC FORMS OF DEOXYCYTIDINE, COMPOSITIONS COMPRISING THE SAME AND USES

(71) Applicant: ZOGENIX MDS, INC., Emeryville, CA (US)

(72) Inventor: Paul Glidden, San Diego, CA (US)

(73) Assignee: ZOGENIX MDS, INC., Emeryville, CA (US)

( * ) Notice: Subject to any disclaimer, the term of this patent is extended or adjusted under 35 U.S.C. 154(b) by 0 days.

(21) Appl. No.: 16/997,727

(22) Filed: Aug. 19, 2020

(65) Prior Publication Data

US 2021/0054014 A1 Feb. 25, 2021

Related U.S. Application Data

(60) Provisional application No. 62/888,893, filed on Aug. 19, 2019.

(51) Int. Cl.
| | | |
|---|---|---|
| *C07H 17/02* | (2006.01) | |
| *A61K 47/02* | (2006.01) | |
| *A61K 47/12* | (2006.01) | |
| *A61K 9/14* | (2006.01) | |

(52) U.S. Cl.
CPC ............ *C07H 17/02* (2013.01); *A61K 47/02* (2013.01); *A61K 47/12* (2013.01); *A61K 9/14* (2013.01); *C07B 2200/13* (2013.01)

(58) Field of Classification Search
None
See application file for complete search history.

(56) References Cited

U.S. PATENT DOCUMENTS

| | | |
|---|---|---|
| 6,936,709 B2 | 8/2005 | Ishibashi et al. |
| 2005/0070711 A1* | 3/2005 | Lifshitz ............... C07D 473/00 544/276 |

FOREIGN PATENT DOCUMENTS

WO WO 2016/205671 12/2016

OTHER PUBLICATIONS

International Search Report from PCT/US2020/047047, dated Dec. 2, 2020.
Bratek-Wiewiorowska, M. D. et al., "Multiforms and behavior of crystalline 2'-deoxycytidine", Journal of Molecular Structure, 1998, vol. 448, pp. 177-183.
Dixit, K. et al., "Quality control of residual solvent content in polymeric microparticles", Journal of Microencapsulation, 2015, vol. 32, No. 2, pp. 107-122.
Wiewiorowski, M. et al., "Monomorphism of cytidine (Cyd) vs. polymorphism of 2'-deoxycytidine (dCyd) Structural and functional consequences," Journal of Molecular Structure, 1997, vol. 436-437, pp. 627-635 abstract; pp. 627-628.

* cited by examiner

*Primary Examiner* — Dale R Miller
(74) *Attorney, Agent, or Firm* — Sterne, Kessler, Goldstein & Fox P.L.L.C.

(57) ABSTRACT

Polymorphic forms of deoxycytidine and methods for preparing the same are provided herein. Also provided are compositions comprising polymorphic forms of deoxycytidine and at least one residual solvent, as well as methods of treating mitochondrial diseases using said compositions.

27 Claims, 3 Drawing Sheets

POLYMORPHIC FORMS OF DEOXYCYTIDINE, COMPOSITIONS COMPRISING THE SAME AND USES

CROSS-REFERENCE TO RELATED APPLICATION

This application claims priority to U.S. Provisional Patent Application No. 62/888,893, filed Aug. 19, 2019, incorporated herein in its entirety.

FIELD OF THE INVENTION

The present invention relates to polymorphic forms of deoxycytidine; compositions comprising polymorphic forms of deoxycytidine and at least one residual solvent in a concentration less than 10% of the ICH limit; and methods of treating diseases or disorders characterized by unbalanced nucleotide pools, especially those found in mitochondrial DNA depletion syndrome, with compositions comprising polymorphic forms of deoxycytidine and at least one residual solvent in a concentration less than 10% of the ICH limit.

BACKGROUND OF THE INVENTION

Polymorphs exist as two or more crystalline phases that have different arrangements and/or different conformations of the molecule in a crystal lattice. When a solvent molecule(s) is contained within the crystal lattice the resulting crystal is called a pseudopolymorph or solvate. If the solvent molecule(s) within the crystal structure is a water molecule, then the pseudopolymorph/solvate is called a hydrate. The polymorphic and pseudopolymorphic solids display different physical properties, including those due to packing, and various thermodynamic, spectroscopic, interfacial and mechanical properties (See H. Brittain, Polymorphism in Pharmaceutical Solids, Marcel Dekker, New York, N.Y., 1999, pp. 1-2). Polymorphic and pseudopolymorphic forms of the drug substance (also known as the "active pharmaceutical ingredient" (API)), as administered by itself or formulated as a drug product (also known as the final or finished dosage form, or as the pharmaceutical composition) are well known and may affect, for example, the solubility, stability, flowability, fractability, and compressibility of drug substances and the safety and efficacy of drug products, (see, e.g., Knapman, K Modem Drug Discoveries, March 2000: 53).

Deoxycytidine (2'-Deoxycytidine, dC), when used in combination with deoxythymidine (dT), is useful for treating certain mitochondrial DNA depletion syndromes. Mitochondrial DNA depletion syndrome (MDS), which is a subgroup of mitochondrial disease, is a frequent cause of severe childhood encephalomyopathy characterized molecularly by reduction of mitochondrial DNA (mtDNA) copy number in tissues and insufficient synthesis of mitochondrial RC complexes (Hirano, et al. 2001). Mutations in several nuclear genes have been identified as causes of infantile MDS, including: TK2, DGUOK, POLG, POLG2, SCLA25A4, MPV17, RRM2B, SUCLA2, SUCLG1, TYMP, OPA1, and ClOorf1 (PEO1). (Bourdon, et al. 2007; Copeland 2008; Elpeleg, et al. 2005; Mandel, et al. 2001; Naviaux and Nguyen 2004; Ostergaard, et al. 2007; Saada, et al. 2003; Sarzi, et al. 2007; Spinazzola, et al. 2006). In addition, mutations in these nuclear genes can also cause multiple deletions of mtDNA with or without mtDNA depletion (Behin, et al. 2012; Garone, et al. 2012; Longley, et al. 2006; Nishino, et al. 1999; Paradas, et al. 2012; Ronchi, et al. 2012; Spelbrink, et al. 2001; Tyynismaa, et al. 2009; Tyynismaa, et al. 2012; Van Goethem, et al. 2001).

One of these genes is TK2, which encodes thymidine kinase (TK2), a mitochondrial enzyme required for the phosphorylation of the pyrimidine nucleosides (thymidine and deoxycytidine) to generate deoxythymidine monophosphate (dTMP) and deoxycytidine monophosphate (dCMP) (Saada, et al. 2001). Mutations in TK2 impair the mitochondrial nucleoside/nucleotide salvage pathways required for synthesis of deoxynucleotide triphosphate (dNTP), the building blocks for mDNA replication and repair.

Patients diagnosed with TK2 deficiency show improvement with administration of a combination of deoxycytidine and deoxythymidine (WO2016205671). The dose administered is relatively high, e.g., 400 mg/kg/day for each of deoxycytidine and deoxythymidine. Accordingly, a 100 kg patient can be administered up to 80 g active (40 g deoxycytidine and 40 g deoxythymidine) per day. The need to minimize the amount of residual solvent resulting from manufacture of the active ingredients is, therefore, critical. Residual solvents include ICH class 1 (i.e., solvent to be avoided), class 2 (i.e., solvent to be limited) and class 3 (i.e., solvent with low toxic potential) solvents. The categorization of solvents according to ICH guidelines is known. The ICH guidelines provide permitted daily exposure (PDE) amounts and concentration limits for class 2 and class 3 residual solvents. Class 1 solvents should not be employed in manufacturing unless unavoidable and the ICH guidelines restrict the concentration of these solvents to very low levels.

Accordingly, there is a need for improved manufacturing processes that provide deoxycytidine compositions with reduced residual solvent content compared to other methods or materials obtained from commercial chemical suppliers.

SUMMARY OF THE INVENTION

In one aspect, the present invention provides Form B deoxycytidine. Form B deoxycytidine has the X-ray powder diffraction (XRPD) pattern illustrated in FIG. 2. In one embodiment, Form B deoxycytidine is characterized by XRPD peaks at 13.7, 17.2, 18.0, 19.2 and 22.8 degrees 2θ (±0.2 degrees 2θ). In a more particular embodiment, the Form B XRPD pattern further comprises one or more peaks at 11.5, 11.8, 13.7, 17.2, 18.0, 19.2, 20.2, 21.1, 21.4, 21.8 and 22.8 degrees 2θ (±0.2 degrees 2θ).

The Form B deoxycytidine of the present invention can be prepared by large-scale manufacturing processes and contains minimal residual solvent. In one embodiment, Form B deoxycytidine has less than about 100 ppm ethyl acetate and/or less than about 100 ppm n-heptane and/or less than about 200 ppm ethanol.

The Form B deoxycytidine of the present invention is stable for at least about 6 months when stored in a sealed container at, e.g. room temperature. Stability can be measured by a number of methods including conversion to Form A deoxycytidine.

The Form B deoxycytidine can be substantially pure, i.e. a mixture comprising Forms of deoxycytidine with about 95% or greater Form B by weight. In another embodiment, isolated Form B is provided.

In another aspect, the present invention provides a method for preparing Form B deoxycytidine comprising (a) providing crude deoxycytidine, (b) contacting the crude deoxycytidine with ethanol to provide a first mixture, (c) distilling ethanol from the first mixture to provide a residue, (d)

contacting the residue with purified water to provide a second mixture, (e) heating the internal temperature of the second mixture to an internal temperature of at least about 40° C., (f) adding ethanol, ethyl acetate and heptane to the second mixture to provide a third mixture, (g) cooling the third mixture to provide Form B deoxycytidine crystals and (h) separating the Form deoxycytidine B crystals from the third mixture.

The manufacturing methods described herein provide deoxycytidine compositions having less residual solvent compared to, e.g., commercial chemical suppliers or previous manufacturing methods. Indeed, the present methods have been optimized to provide deoxycytidine compositions with less than about 10% of the class 2 and class 3 residual solvent concentrations permitted by the ICH guidelines. The methods also provide deoxycytidine compositions with undetectable levels of certain class 1 solvents, e.g. 1,2-dichloroethane, according to validated methods In one aspect, a composition comprises Form B deoxycytidine and at least one residual solvent selected from ICH class 2 and class 3 solvents, wherein the concentration of the at least one residual solvent is less than about 10% of the ICH concentration limit for each residual solvent. Preferred class 2 and class 3 residual solvents include methanol, toluene, methylene chloride, ethanol, tert-butylmethyl ether (TBME), acetone, ethyl acetate, and n-heptane.

In a particular embodiment, a composition comprises Form B deoxycytidine and at least one of the following: (a) from 1 ppm to about 300 ppm methanol, (b) from 1 ppm to about 89 ppm toluene, (c) from 1 ppm to about 600 ppm methylene chloride, (d) from 1 ppm to about 500 ppm ethanol, (e) from 1 ppm to about 500 ppm TBME, (f) from 1 ppm to about 500 ppm acetone, (g) from 1 ppm to about 500 ppm ethyl acetate, and (h) from 1 ppm to about 500 ppm n-heptane.

In another particular embodiment, a composition comprises Form B deoxycytidine and not more than 300 ppm methanol, not more than 89 ppm toluene, not more than 60 ppm methylene chloride, not more than 500 ppm ethanol, not more than 500 ppm TBME, not more than 500 ppm acetone, not more than 500 ppm ethyl acetate and not more than 500 ppm n-heptane.

In preferred embodiments, the compositions have undetectable levels of class 1 solvents, in particular 1,2-dichloroethane.

In still another aspect, pharmaceutical compositions comprising substantially pure Form B deoxycytidine and at least one pharmaceutically acceptable carrier are provided. The pharmaceutical composition can also further comprise deoxythymidine.

In one embodiment, a pharmaceutical composition comprises Form B deoxycytidine, at least one residual solvent, and at least one pharmaceutically acceptable carrier, wherein the at least one residual solvent is selected from ICH class 2 and class 3 solvents and the concentration of the at least one residual solvent is less than about 10% of the ICH concentration limit for each residual solvent.

In a particular embodiment, a pharmaceutical composition comprises Form B deoxycytidine, at least one pharmaceutically acceptable carrier and at least one of the following:

(a) from 1 ppm to about 300 ppm methanol, (b) from 1 ppm to about 89 ppm toluene, (c) from 1 ppm to about 60 ppm methylene chloride, (d) from 1 ppm to about 500 ppm ethanol, (e) from 1 ppm to about 500 ppm TBME, (f) from 1 ppm to about 500 ppm acetone, (g) from 1 ppm to about 500 ppm ethyl acetate, and (h) from 1 ppm to about 500 ppm n-heptane.

In another particular embodiment, a pharmaceutical composition comprises not more than 300 ppm methanol, not more than 89 ppm toluene, not more than 60 ppm methylene chloride, not more than 500 ppm ethanol, not more than 500 ppm TBME, not more than 500 ppm acetone, not more than 500 ppm ethyl acetate and not more than 500 ppm n-heptane.

In preferred embodiments, the pharmaceutical compositions have undetectable levels of class 1 solvents, in particular 1,2-dichloroethane.

In another embodiment, a fixed-dose powder pharmaceutical composition is provided comprising Form B deoxycytidine, deoxythymidine, at least one residual solvent and at least one pharmaceutically acceptable carrier, wherein the at least one residual solvent is selected from ICH class 2 and class 3 solvents and the concentration of the at least one residual solvent is less than about 10% of the ICH concentration limit for each residual solvent. The fixed-dose powder pharmaceutical composition preferably has undetectable levels of class 1 solvents, in particular 1,2-dichloroethane.

In yet another aspect, a method of treating a disease or disorder characterized by an unbalanced nucleotide pool is provided. Said method comprises administering to a subject in need thereof a therapeutically effective amount of composition described herein. In a particular embodiment, the disorder is a thymidine kinase 2 deficiency, characterized by mutation(s) in the TK2 gene.

In one embodiment, a composition comprising Form B deoxycytidine and at least one residual solvent is administered to the subject, wherein the at least one residual solvent is selected from ICH class 2 and class 3 solvents and the concentration of the at least one residual solvent is less than about 10% of the ICH concentration limit for each residual solvent. The composition can be a pharmaceutical composition that further comprises at least one pharmaceutically acceptable carrier.

The method can further comprise administering to the subject a therapeutically effective amount of a second composition comprising deoxythymidine. The second composition can be a pharmaceutical composition that further comprises at least one pharmaceutically acceptable carrier. In such embodiments, the combined residual solvent content in the first and second compositions for each residual solvent is less than about 10% of the ICH concentration limit for each residual solvent.

In other embodiments, one composition is administered comprises Form B deoxycytidine, deoxythymidine and at least one residual solvent, wherein the at least one residual solvent is selected from ICH class 2 and class 3 solvents and the concentration of the at least one residual solvent is less than about 10% of the ICH concentration limit for each residual solvent. The composition can be a pharmaceutical composition that further includes at least one pharmaceutically acceptable carrier. The composition can be the fixed-dosed powder pharmaceutical composition described herein.

DETAILED DESCRIPTION OF THE INVENTION

I. Forms of Deoxycytidine

Figure 1:
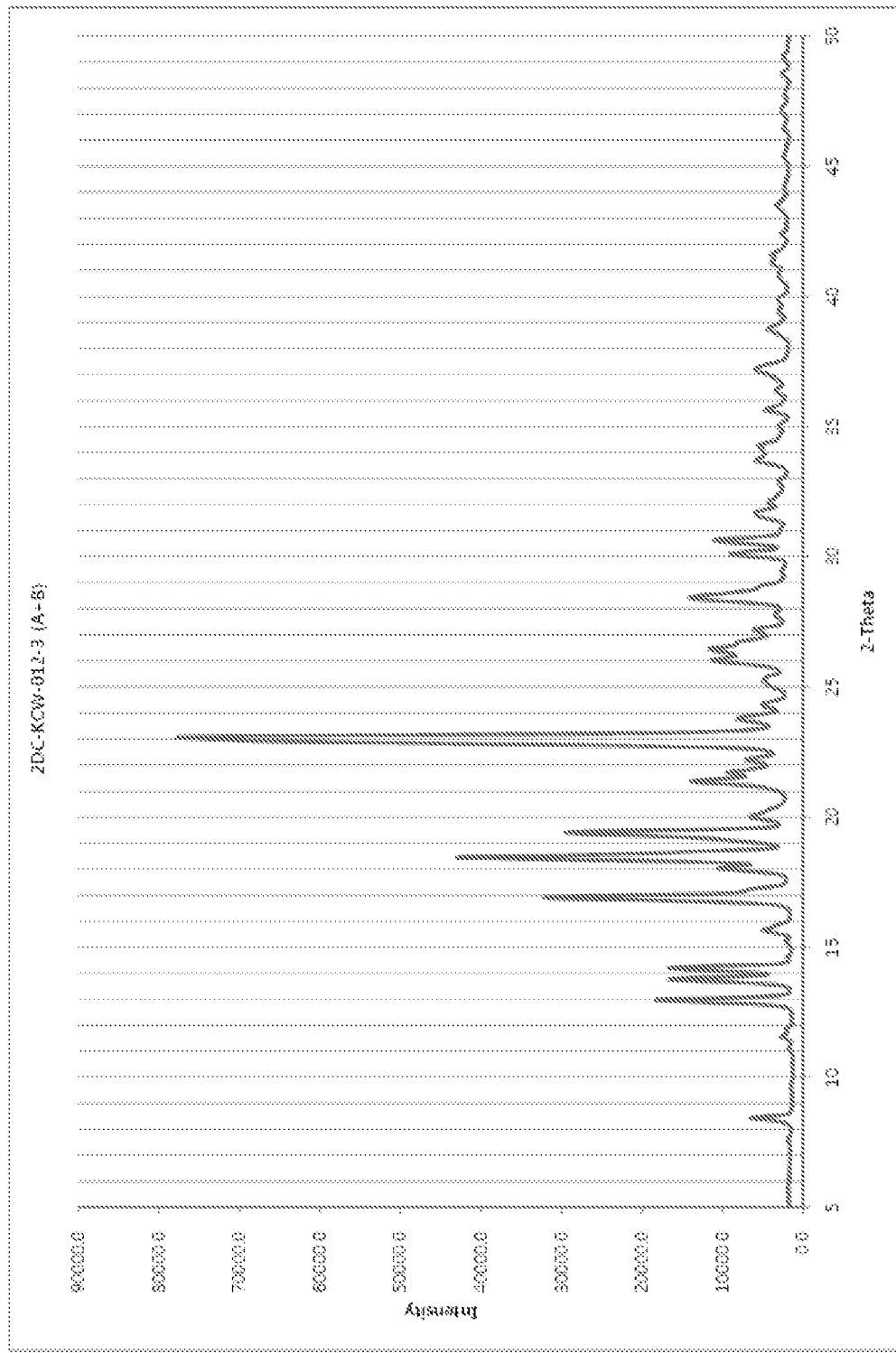
FIG. 1: illustrates the X-ray diffraction pattern of a mixture of Form A and Form B deoxycytidine.

The present invention provides crystalline forms of deoxycytidine and compositions comprising crystalline forms of deoxycytidine.

In one embodiment, Form B deoxycytidine is provided. The powder X-ray diffraction (XRPD) pattern for Form B deoxycytidine is provided in FIG. 2. Form B deoxycytidine is characterized by a XRPD pattern comprising peaks at 13.7, 17.2, 18.0, 19.2 and 22.8 degrees 2θ (±0.2 degrees 2θ). In a more particular embodiment, Form B is characterized by a XRPD pattern comprising peaks at 13.7, 17.2, 18.0, 19.2 and 22.8 degrees 2θ (±0.1 degrees 2θ). The XRPD is preferably made using CuK$_{\alpha1}$ radiation.

The Form B XRPD pattern can further comprise one or more peaks at 11.5, 11.8, 20.2, 21.1, 21.4 and 21.8 degrees 2θ (±0.2 degrees 2θ). In a more particular embodiment, the XRPD pattern can further comprise one or more peaks at 11.5, 11.8, 20.2, 21.1, 21.4 and 21.8 degrees 2θ (±0.1 degrees 2θ).

In a particular embodiment, Form B deoxycytidine is characterized by a XRPD pattern comprising peaks at 11.5, 11.8, 13.7, 17.2, 18.0, 19.2, 20.2, 21.1, 21.4, 21.8 and 22.8 degrees 2θ (±0.2 degrees 2θ). In an even more particular embodiment, Form B deoxycytidine is characterized by a XRPD pattern comprising peaks at 11.5, 11.8, 13.7, 17.2, 18.0, 19.2, 20.2, 21.1, 21.4, 21.8 and 22.8 degrees 2θ (±0.1 degrees 2θ).

In one embodiment, Form B deoxycytidine is provided in substantially pure form. "Substantially pure", as used herein, refers to a mixture of Forms of deoxycytidine comprising about 95% or greater Form B by weight, about 96% or greater Form B by weight, about 97% or greater Form B by weight, about 98% or greater Form B or about 99% or greater Form B by weight.

Form B deoxycytidine can also be provided in isolated form, i.e. 100% Form B.

Form B deoxycytidine contains minimal residual solvent from manufacturing.

In one embodiment, Form B deoxycytidine comprises less than about 100 ppm ethyl acetate, such as, for example, less than about 90 ppm, less than about 80 ppm, less than about 60 ppm or less than about 50 ppm. In another embodiment, Form B deoxycytidine comprises from 1 ppm to about 100 ppm ethyl acetate, such as, for example, from 1 ppm to about 90 ppm, from 1 ppm to about 80 ppm, from 1 ppm to about 60 ppm and from 1 ppm to about 50 ppm.

Form B deoxycytidine comprises less than about 100 ppm n-heptane, preferably less than about 90 ppm, less than about 80 ppm, less than about 70 ppm, less than about 60 ppm, less than about 50 ppm, less than about 40 ppm or less than about 30 ppm. In another embodiment, Form B deoxycytidine comprises from 1 ppm to about 100 ppm n-heptane, such as, for example, from 1 ppm to about 90 ppm, from 1 ppm to about 80 ppm, from 1 ppm to about 70 ppm, from 1 ppm to about 60 ppm, from 1 ppm to about 50 ppm, from 1 ppm to about 40 ppm and from 1 ppm to about 30 ppm.

Form B deoxycytidine comprises less than about 200 ppm ethanol, preferably less than about 150 ppm ethanol. In another embodiment, Form B deoxycytidine comprises from 1 ppm to about 200 ppm ethanol, such as, for example, from 1 ppm to about 150 ppm, from 1 ppm to about 125 ppm, from 1 ppm to about 100 ppm, from 1 ppm to about 75 ppm, from 1 ppm to about 50 ppm and from 1 ppm to about 25 ppm.

In a particular embodiment, Form B deoxycytidine comprises less than about 100 ppm ethyl acetate, less than about 100 ppm n-heptane and less than about 200 ppm ethanol. Form B deoxycytidine can comprise from 1 ppm to about 100 ppm ethyl acetate, from 1 ppm to about 100 ppm n-heptane and from 1 ppm to about 200 ppm ethanol. In another embodiment, Form B deoxycytidine has at least one of the following: (a) from 1 ppm to about 100 ppm ethyl acetate, (b) from 1 ppm to about 100 ppm n-heptane or (c) from 1 ppm to about 200 ppm ethanol.

In another particular embodiment, Form B deoxycytidine comprises less than about 70 ppm ethyl acetate, less than about 50 ppm n-heptane and less than about 200 ppm ethanol. Form B deoxycytidine can comprise from 1 ppm to about 70 ppm ethyl acetate, from 1 ppm to about 50 ppm n-heptane and from 1 ppm to about 200 ppm ethanol. In another embodiment, Form B deoxycytidine comprises at least one of the following: (a) from 1 ppm to about 70 ppm ethyl acetate, (b) from 1 ppm to about 50 ppm n-heptane or (c) from 1 ppm to about 200 ppm ethanol.

Form B deoxycytidine is stable for at least about 6 months when stored in a sealed container at, e.g. room temperature, more particularly the Form B deoxycytidine is stable for at least about 12 months or at least about 18 months.

"Stability", as used herein, can be measured by confirming the Form B XRPD pattern of the material after a given storage time. Conversion of Form B to Form A deoxycytidine, as determined by)(RFD, indicates instability. Stability can also be measured by confirming compliance with the test attribute standards as outlined in Example 4. Test attributes include physical appearance, IR trace, HPLC trace for active and impurities, water content, residual solvent content, elemental impurities and microbial growth. One or more of these attributes can be measured after storage over a given period of time, e.g. 6 months, 12 months or more, and under various conditions, e.g. 25±2° C./60±5% relative humidity or 40±2° C./75±5% relative humidity).

A method for preparing Form B deoxycytidine is provided in Example 1.

In one embodiment, a method for preparing Form B deoxycytidine comprises (a) providing crude deoxycytidine, (b) contacting the crude deoxycytidine with ethanol to provide a first mixture, (c) distilling ethanol from the first mixture to provide a residue, (d) contacting the residue with purified water to provide a second mixture, (e) heating the internal temperature of the second mixture to an internal temperature of at least about 40° C., (f) adding ethanol, ethyl acetate and heptane to the second mixture to provide a third mixture, (g) cooling the third mixture to provide Form B deoxycytidine crystals and (h) separating the Form deoxycytidine B crystals from the third mixture.

The present method can be used in large scale manufacturing, e.g. for producing deoxycytidine batches greater than about 75 kg, such as, for example, greater than about 100 kg, greater than about 125 kg, greater than about 150 kg or greater than about 200 kg.

The crude deoxycytidine may comprise a mixture of Form A and Form B polymorphic forms in an amount that equals about 100%. In one embodiment, the crude deoxycytidine comprises at least about 5% Form B, at least about 10% Form B, at least about 20% Form B, at least about 30% Form B, at least about 40% Form B, at least about 50% Form B, at least about 60% Form B, at least about 70% Form B, at least about 80% Form B or at least about 10% Form B. In another embodiment, the crude deoxycytidine comprises at least about 5% Form A, at least about 10% Form A, at least about 20% Form A, at least about 30% Form A, at least about 40% Form A, at least about 50% Form A, at least about 60% Form A, at least about 70% Form A, at least about 80% Form A or at least about 10% Form A.

The distillation in step (c) preferably takes place a temperature that does not exceed about 70° C., such as, for example, at a temperature from about 40° C. to less than about 70° C.

The amount of water used in (d) is preferably from about 0.10 to about 0.5 volumes, such as 0.25 volumes.

The internal temperature of the second mixture in (e) is preferably from about 40° C. to about 50° C.

The solvents in addition step (f) can be added in any order and can be added at once or in parts. In one embodiment, ethanol is added first, followed by a mixture of ethanol, ethyl acetate and n-heptane. The amount of ethanol, ethyl acetate and n-heptane can vary. The amount of ethanol can be 1 volume, 2 volumes or 3 volumes. The amount of ethyl acetate can be 1 volume, 2 volumes or 3 volumes. The amount of n-heptane can be 1 volume, 2 volumes or 3 volumes. The solvent or mixtures of solvents is generally added dropwise or slow enough to prevent crash precipitation.

The third mixture in (g) can be cooled in a step-wise or gradient fashion. In one embodiment, the third mixture is cooled to an internal temperature from about 20° C. to about 30° C., maintained for at that temperature for a period of time with agitation, and then cooled further. In a more particular embodiment, the third mixture is agitated for at least about 1 hour, at least about 3 hours, at least about 6 hours, at least about 12 hours, or at least about 24 hours before further cooling. After agitation, the mixture can be further cooled to an internal temperature from about 0° C. to about 10° C.

Separation step (h) can be performed by any suitable separation means, e.g. centrifugal filtration, gravity filtration or vacuum filtration.

The method provides a composition comprising substantially pure Form B deoxycytidine.

The Form B crystals obtained by the methods herein may contain at least one residual solvent and can therefore be categorized as a composition.

The compositions can further contain one or more polymorphic forms of deoxycytidine in addition to Form B, e.g. Form A or other polymorphic forms, including hydrated polymorph forms. In one embodiment, a composition comprises up to about 10% by weight of the one or more other polymorphic forms of deoxycytidine, such as, for example, from about 0.5% to about 10%, from about 1% to about 10%, from about 1% to about 5% or from about 1% to about 3%.

Compositions comprising Form B deoxycytidine prepared by the method described herein contain at least one residual solvent. The solvent can belong to ICH class 2 (i.e., solvent to be limited) or class 3 (i.e., solvent with low toxic potential). The ICH permitted daily exposure (PDE) amounts and concentration limits for class 2 solvents are provided in the table below. Class 3 solvents are regarded as less toxic and of lower human risk to human health. The ICH guideline for class 3 solvents is 5,000 ppm concentration or 50 mg per day or less.

TABLE 1

Class 2 solvents in pharmaceutical products.

| Solvent | Permitted Daily Exposure (PDE) mg/day | Concentration limit (ppm) |
|---|---|---|
| Acetonitrile | 4.1 | 410 |
| Chlorobenzene | 3.6 | 360 |
| Chloroform | 0.6 | 60 |
| Cumene | 0.7 | 70 |
| Cyclohexane | 38.8 | 3880 |
| 1,2-Dichloroethene | 18.7 | 1870 |
| Dichloromethane | 6.0 | 600 |
| 1,2-Dimethoxyethane | 1.0 | 100 |
| N,N-Dimethylacetamide | 10.9 | 1090 |
| N,N-Dimethylformamide | 8.8 | 880 |
| 1,4-Dioxane | 3.8 | 380 |
| 2-Ethoxyethanol | 1.6 | 160 |
| Ethyleneglycol | 6.2 | 620 |
| Formamide | 2.2 | 220 |
| Hexane | 2.9 | 290 |
| Methanol | 30.0 | 3000 |
| 2-Methoxyethanol | 0.5 | 50 |
| Methylbutyl ketone | 0.5 | 50 |
| Methylcyclohexane | 11.8 | 1180 |
| Methylisobutylketone | 45 | 4500 |
| N-Methylpyrrolidone | 5.3 | 530 |
| Nitromethane | 0.5 | 50 |
| Pyridine | 2.0 | 200 |
| Sulfolane | 1.6 | 160 |
| Tetrahydrofuran | 7.2 | 720 |
| Tetralin | 1 | 100 |
| Toluene | 8.9 | 890 |
| 1,1,2-Trichloroethene | 0.8 | 80 |
| Xylene | 21.7 | 2170 |

Class 1 solvents are solvents to be avoided. ICH guidelines state that class 1 solvents should not be employed in the manufacture of drug substances because of unacceptable toxicity or deleterious environmental impact. However, they are permitted in restricted amounts if unavoidable. The ICH concentration limits for class 1 solvents are provided in the table below.

TABLE 2

Class 1 Solvents in Pharmaceutical Products

| Solvent | Concentration limit (ppm) | Concern |
|---|---|---|
| Benzene | 2 | Carcinogen |
| Carbon tetrachloride | 4 | Toxic and environmental hazard |
| 1,2-Dichloroethane | 5 | Toxic |
| 1,1-Dichloroethene | 8 | Toxic |
| 1,1,1-Trichloroethane | 1,500 | Environmental hazard |

The manufacturing methods described herein provide deoxycytidine compositions having substantially less residual solvent concentrations compared to, e.g., commercial chemical suppliers or previously known manufacturing methods. Indeed, the present methods have been optimized to provide deoxycytidine compositions with (a) no more than about 10% of the concentration/amount of class 2 and class 3 residual solvent permitted by the ICH guidelines and (b) undetectable levels of ICH class 1 solvents, in particular 1,2-dichloroethane.

"Undetectable", as used herein, refers to a concentration of a substance that is below the limit of detection for that substance when measured using standard, validated methods. Such methods are known in the art and include, e.g. the gas chromatography (GC) methods provided in the United States Pharmacopeial (USP) chapter on residual solvents (467) and the European Pharmacopoeia (Ph. Eur). The limit of detection for 1,2-dichloroethane, for example, is 0.2 ppm.

In one embodiment, a composition comprises Form B deoxycytidine and at least one residual solvent, such as, for example, one residual solvent, two residual solvents, three residual solvents, four residual solvents, five residual solvents, or six or more residual solvents.

In one embodiment, a composition comprises Form B deoxycytidine and at least one residual solvent, wherein the at least one residual solvent is selected from ICH class 2 and class 3 solvents and the concentration of the at least one residual solvent is less than about 10% of the ICH concentration limit for each residual solvent. In a more particular embodiment, a composition consists of Form B deoxycytidine and at least one residual solvent, wherein the at least one residual solvent is selected from ICH class 2 and class 3 solvents and the concentration of the at least one residual solvent is less than about 10% of the ICH concentration limit for the particular residual solvent.

Preferred class 2 and class 3 residual solvents include methanol, toluene, methylene chloride, ethanol, tert-butylmethyl ether, acetone, ethyl acetate, and n-heptane.

Methanol is an ICH class 2 solvent with a 30 mg permitted daily exposure (PDE) or 3,000 ppm concentration limit. Compositions of the present invention may contain methanol in a concentration from 1 ppm to about 300 ppm, such as, for example, from 1 ppm to about 250 ppm, from 1 ppm to about 200 ppm, from 1 ppm to about 150 ppm, from 1 ppm to about 100 ppm, from 1 ppm to about 50 ppm or from 1 ppm to about 25 ppm.

Toluene is an ICH class 2 solvent with a PDE of 8.9 mg/day or 890 ppm concentration limit. Compositions of the present invention may contain toluene in a concentration from 1 ppm to about 89 ppm, such as, for example, from 1 ppm to about 45 ppm, from 1 ppm to about 25 ppm and from 1 ppm to about 10 ppm.

Methylene chloride (dichloromethane) is an ICH class 2 solvent with a PDE of 6.0 mg/day or 600 ppm concentration limit. Compositions of the present invention may contain methylene chloride in a concentration from 1 ppm to about 60 ppm, such as, for example, from 1 ppm to about 50 ppm, from 1 ppm to about 40 ppm, from 1 ppm to about 30 ppm, from 1 ppm to about 20 ppm, from 1 ppm to about 10 ppm and from 1 ppm to about 5 ppm.

Ethanol is an ICH class 3 solvent with a PDE of 50 mg/day or 5,000 ppm concentration limit. Compositions of the present invention may contain ethanol in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

Tert-butylmethyl ether (TBME) is an ICH class 3 solvent with a PDE of 50 mg/day or 5,000 ppm concentration limit. Compositions of the present invention may contain tert-butylmethyl ether in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

Acetone is an ICH class 3 solvent with a PDE of 50 mg/day or 5,000 ppm concentration limit. Compositions of the present invention contain may acetone in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

Ethyl acetate is an ICH class 3 solvent with a PDE of 50 mg/day or 5,000 ppm concentration limit. Compositions of the present invention may contain ethyl acetate in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

n-Heptane is an ICH class 3 solvent with a 50 mg PDE or 5,000 ppm limit. Compositions of the present invention may contain n-heptane in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

In a particular embodiment, a composition comprises Form B deoxycytidine and at least one of the following class 2 and/or class 3 ICH solvents: (a) from 1 ppm to about 300 ppm methanol, (b) from 1 ppm to about 89 ppm toluene, (c) from 1 ppm to about 60 ppm methylene chloride, (d) from 1 ppm to about 500 ppm ethanol, (e) from 1 ppm to about 500 ppm TBME, (f) from 1 ppm to about 500 ppm acetone, (g) from 1 ppm to about 500 ppm ethyl acetate, and (h) from 1 ppm to about 500 ppm n-heptane.

1,2-dichloroethane (1,2-DCE) is an ICH class 1 solvent with a concentration limit of 5 ppm. Compositions of the present invention may contain 1,2-DCE in a concentration from 0.2 ppm to about 0.2 ppm to about 0.5 ppm, preferably below 0.2 ppm whereby it is undetectable.

The compositions comprising Form B deoxycytidine and at least one residual solvent provided herein are stable for a period of at least 6 months, such as, for example, a least 9 months, at least 12 months, or at least 24 months. Stability of the compositions can be measured in accordance with Example 4, i.e., confirming compliance with test attributes when subjected to storage conditions.

Figure 3:
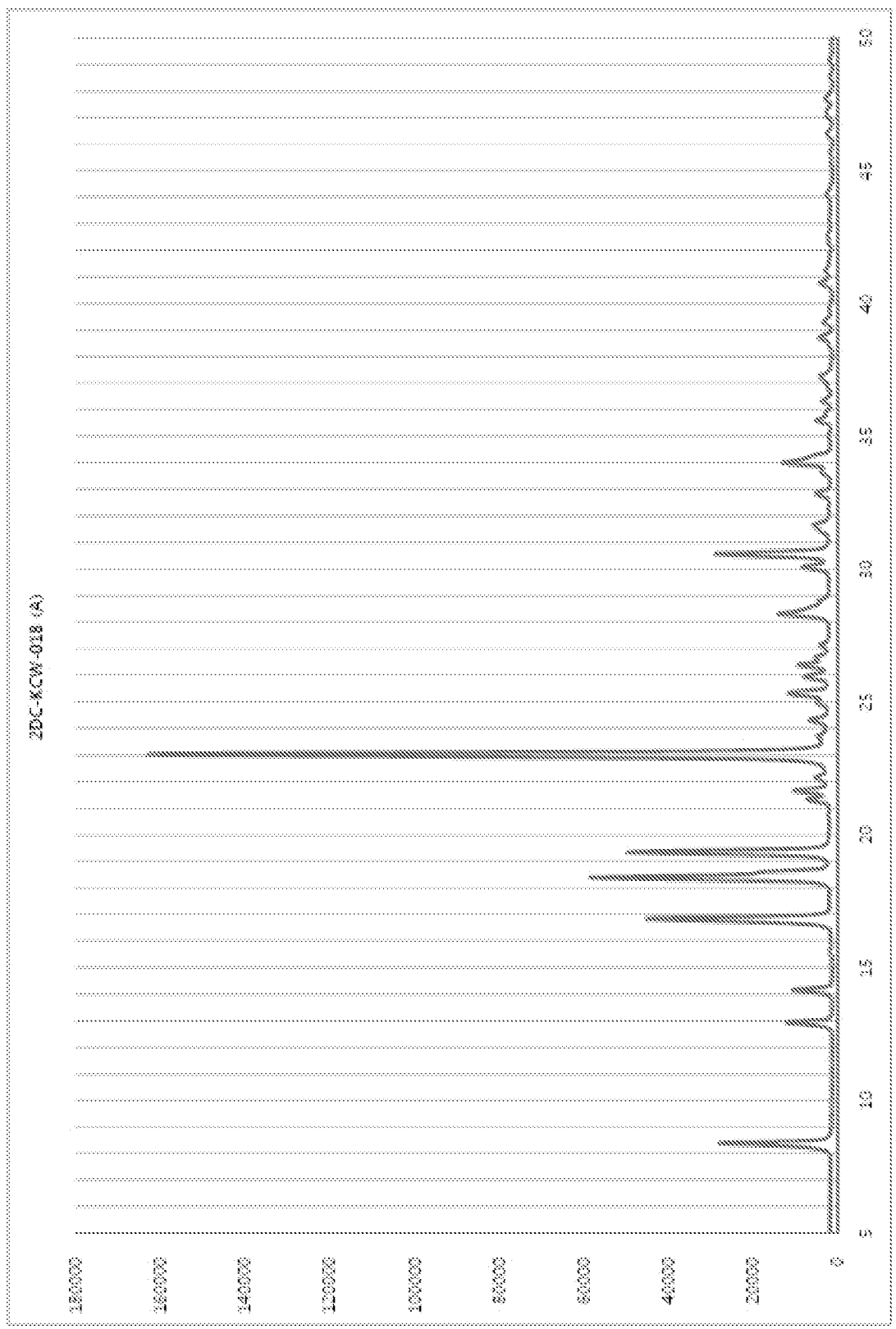
FIG. 3: illustrates the X-ray diffraction pattern of Form A deoxycytidine.

In another embodiment, Form A deoxycytidine is provided. The XRPD pattern for Form A deoxycytidine is provided in FIG. 3. Form A deoxycytidine is characterized by a XRPD pattern comprising peaks at 8.4, 12.9, 14.2, 16.8, 18.4, 19.4, 28.4, 30.0 and 30.6 degrees 2θ (±0.2 degrees 2θ). In a more particular embodiment, Form A is characterized by a XRPD pattern comprising peaks at 8.4, 12.9, 14.2, 16.8, 18.4, 19.4, 28.4, 30.0 and 30.6 degrees 2θ (±0.1 degrees 2θ). The XRPD is preferably made using $CuK_{\alpha 1}$ radiation.

The Form A XRPD pattern can further comprise one or more peaks at 21.3, 21.6 and 22.2 degrees 2θ (±0.2 degrees 2θ). In a more particular embodiment, the XRPD pattern can further comprise one or more peaks at 21.3, 21.6 and 22.2 degrees 2θ (±0.1 degrees 2θ).

In one embodiment, Form A deoxycytidine is provided in substantially pure form. "Substantially pure", as used herein, refers to a mixture of Forms of deoxycytidine comprising about 95% or greater Form A by weight, about 96% or greater Form A by weight, about 97% or greater Form A by weight, about 98% or greater Form A or about 99% or greater Form A by weight.

II. Pharmaceutical Compositions

The present invention also provides a pharmaceutical composition comprising a substantially pure form of deoxycytidine described herein as an active ingredient and at least one pharmaceutically acceptable carrier.

In one embodiment, a pharmaceutical composition comprises substantially pure Form B deoxycytidine as an active ingredient, at least one residual solvent and at least one pharmaceutically acceptable carrier.

In another embodiment, a pharmaceutical composition comprises a mixture of substantially pure Form B deoxycytidine and deoxythymidine, where deoxythymidine also acts as an active ingredient, at least one residual solvent and at least one pharmaceutically acceptable carrier.

In still another embodiment, a pharmaceutical composition comprises a composition comprising Form B deoxycytidine described herein and at least one pharmaceutically acceptable carrier.

In yet another embodiment, a pharmaceutical composition comprises a composition comprising Form B deoxycytidine described herein, a composition comprising deoxythymidine, and at least one pharmaceutically acceptable carrier.

The composition comprising deoxythymidine contains deoxythymidine in an amount of at least 97% by weight, such as, from about 97-99 wt % deoxythymidine or 98-99 wt % deoxythymidine. The remainder can be one or more impurities, including at least one residual solvent.

Such pharmaceutical compositions comprise a therapeutically effective amount of the Form B deoxycytidine (and, if applicable, a therapeutically effective amount of deoxythymidine) and at least one pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel (silica colloidal anhydrous), magnesium stearate, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

The pharmaceutical composition can include at least one glidant. Glidants are substances to counteract the poor flowability of powders during manufacturing processes. Exemplary glidants include, but are not limited to, colloidal silica, such as colloidal silicon dioxide, e.g., AEROSIL, magnesium (Mg) trisilicate, powdered cellulose, starch, talc and tribasic calcium phosphate.

The pharmaceutical compositions can include at least one lubricant. Lubricants are substances that reduce friction between particles. Exemplary lubricants include, but are not limited to, magnesium stearate, aluminum (Al) or Ca stearate, PEG 4000 to 8000 and talc, hydrogenated castor oil, stearic acid and salts thereof, glycerol esters and Na-stearyl-fumarate, hydrogenated cotton seed oil.

In a particular aspect, a fixed-dose pharmaceutical composition comprises Form B deoxycytidine, deoxythymidine, at least one residual solvent, at least one glidant and at least one lubricant, wherein the composition is in the form of a powder.

The amount of Form B deoxycytidine in the pharmaceutical composition can be from 1,000 mg to about 5,000 mg, such as, for example, from about 1,000 mg to about 4,000 mg, from about 1,000 mg to about 3,000 mg or from about 1,000 mg to about 2,000 mg.

The amount of deoxythymidine in the pharmaceutical composition can be from 1,000 mg to about 5,000 mg, such as, for example, from about 1,000 mg to about 4,000 mg, from about 1,000 mg to about 3,000 mg or from about 1,000 mg to about 2,000 mg.

In a preferred embodiment, both Form B deoxycytidine and deoxythymidine are present in about 2,000 mg.

The ratio of deoxycytidine to deoxythymidine can vary. For example, they can be in a ratio of 50/50, or in ratios of about 5/95, 10/90, 15/85, 20/80, 25/75, 30/70, 35/65, 40/60, 45/55, 55/45, 60/40, 65/35, 70/30, 75/25, 80/20, 85/15, 90/10, and 95/5.

The at least one glidant can be present in an amount from about 0.1 wt % to about 10 wt %, such as, for example, from about 1% to about 5% or about 1% to about 3%. In a preferred embodiment, the glidant is colloidal silicon dioxide (e.g. AEROSIL 200).

The at least one lubricant can be present in an amount from about 0.1 wt % to about 1 wt %, such as, for example, from about 0.1% to about 0.5% or from about 0.3% to about 0.7%. In a preferred embodiment, the lubricant is Mg stearate.

Form B deoxycytidine can be present in an amount from about 40 wt % to about 60 wt %, such as, for example, from about 40 wt % to about 50 wt %, from about 50 wt % to about 60 wt %, or from about 45 wt % to about 55 wt %.

Similarly, deoxythymidine can be present in an amount from about 40 wt % to about 60 wt %, such as, for example, from about 40 wt % to about 50 wt %, from about 50 wt % to about 60 wt %, or from about 45 wt % to about 55 wt %.

The powder pharmaceutical composition is packaged in any suitable form, e.g., a bottle, pouch or sachet. In a preferred embodiment, the pharmaceutical composition is packaged in a pouch constructed of laminated PET, aluminum and low-density polyethylene. An oral solution is then prepared by dissolving the powder pharmaceutical composition in water prior to administration.

The at least one residual solvent can be a carry-over from manufacturing of either the Form B deoxycytidine (as described above), the pharmaceutically acceptable carrier or, if applicable, the deoxythymidine.

The pharmaceutical composition contains at least one residual solvent, such as, for example, two residual solvents, three residual solvents, four residual solvents or five or more residual solvents.

The at least one residual solvent is selected from ICH class 2 and class 3 solvents and the concentration of the at least one residual solvent is less than about 10% of the ICH concentration limit for each residual solvent.

Preferred class 2 and class 3 residual solvents include methanol, toluene, methylene chloride, ethanol, tert-butyl-methyl ether, acetone, ethyl acetate, and n-heptane.

Methanol is an ICH class 2 solvent with a 30 mg permitted daily exposure (PDE) or 3,000 ppm concentration limit. Pharmaceutical compositions of the present invention may contain methanol in a concentration from 1 ppm to about 300 ppm, such as, for example, from 1 ppm to about 250 ppm, from 1 ppm to about 200 ppm, from 1 ppm to about 150 ppm, from 1 ppm to about 100 ppm, from 1 ppm to about 50 ppm or from 1 ppm to about 25 ppm.

Toluene is an ICH class 2 solvent with a PDE of 8.9 mg/day or 890 ppm concentration limit. Pharmaceutical compositions of the present invention may contain toluene in a concentration from 1 ppm to about 89 ppm, such as, for example, from 1 ppm to about 45 ppm, from 1 ppm to about 25 ppm and from 1 ppm to about 10 ppm.

Methylene chloride (dichloromethane) is an ICH class 2 solvent with a PDE of 6.0 mg/day or 600 ppm concentration limit. Pharmaceutical compositions of the present invention may contain methylene chloride in a concentration from 1 ppm to about 60 ppm, such as, for example, from 1 ppm to about 50 ppm, from 1 ppm to about 40 ppm, from 1 ppm to about 30 ppm, from 1 ppm to about 20 ppm, from 1 ppm to about 10 ppm and from 1 ppm to about 5 ppm.

Ethanol is an ICH class 3 solvent with a PDE of 50 mg/day or 5,000 ppm concentration limit. Pharmaceutical compositions of the present invention may contain ethanol in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

Tert-butylmethyl ether (TBME) is an ICH class 3 solvent with a PDE of 50 mg/day or 5,000 ppm concentration limit. Pharmaceutical compositions of the present invention may contain tert-butylmethyl ether in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

Acetone is an ICH class 3 solvent with a PDE of 50 mg/day or 5,000 ppm concentration limit. Pharmaceutical compositions of the present invention contain may acetone in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

Ethyl acetate is an ICH class 3 solvent with a PDE of 50 mg/day or 5,000 ppm concentration limit. Pharmaceutical compositions of the present invention may contain ethyl acetate in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

n-Heptane is an ICH class 3 solvent with a 50 mg PDE or 5,000 ppm limit. Pharmaceutical compositions of the present invention may contain n-heptane in a concentration from 1 ppm to about 500 ppm, such as, for example, from 1 ppm to about 400 ppm, from 1 ppm to about 300 ppm, from 1 ppm to about 200 ppm, from 1 ppm to about 100 ppm and from 1 ppm to about 50 ppm.

In a particular embodiment, a pharmaceutical composition described herein comprises at least one of the following: (a) from 1 ppm to about 300 ppm methanol, (b) from 1 ppm to about 89 ppm toluene, (c) from 1 ppm to about 60 ppm methylene chloride, (d) from 1 ppm to about 500 ppm ethanol, (e) from 1 ppm to about 500 ppm TBME, (f) from 1 ppm to about 500 ppm acetone, (g) from 1 ppm to about 500 ppm ethyl acetate, and (h) from 1 ppm to about 500 ppm n-heptane.

In another particular embodiment, a pharmaceutical composition comprises Form B deoxycytidine, deoxythymidine, at least one pharmaceutically acceptable carrier and at least one of the following: (a) from 1 ppm to about 300 ppm methanol, (b) from 1 ppm to about 89 ppm toluene, (c) from 1 ppm to about 60 ppm methylene chloride, (d) from 1 ppm to about 500 ppm ethanol, (e) from 1 ppm to about 500 ppm TBME, (f) from 1 ppm to about 500 ppm acetone, (g) from 1 ppm to about 500 ppm ethyl acetate, and (h) from 1 ppm to about 500 ppm n-heptane.

1,2-dichloroethane (1,2-DCE) is an ICH class 1 solvent with a concentration limit of 5 ppm. Compositions of the present invention may contain 1,2-DCE in a concentration from 0.2 ppm to about 0.5 ppm, preferably below 0.2 ppm whereby it is undetectable.

Oral administration is a preferred method of administration. The active ingredients can be added to any form of liquid a patient would consume including but not limited to, milk, both cow's and human breast, infant formula, and water.

Additionally, pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

In order to overcome any issue of crossing the blood/brain barrier, intrathecal administration is a further preferred form of administration. Intrathecal administration involves injection of the drug into the spinal canal, more specifically the subarachnoid space such that it reaches the cerebrospinal fluid. This method is commonly used for spinal anesthesia, chemotherapy, and pain medication. Intrathecal administration can be performed by lumbar puncture (bolus injection) or by a port-catheter system (bolus or infusion). The catheter is most commonly inserted between the laminae of the lumbar vertebrae and the tip is threaded up the thecal space to the desired level (generally L3-L4). Intrathecal formulations most commonly use water, and saline as excipients but EDTA and lipids have been used as well.

A further preferred form of administration is parenteral including intravenous administration. Pharmaceutical compositions adapted for parenteral administration, including intravenous administration, include aqueous and non-aqueous sterile injectable solutions or suspensions, which may contain anti-oxidants, buffers, bacteriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Additionally, since some patients may be receiving enteral nutrition by the time the deoxy nucleoside treatment begins, the dNs can be administered through a gastronomy feeding tube or other enteral nutrition means.

Further methods of administration include mucosal, such as nasal, sublingual, vaginal, buccal, or rectal; or transdermal administration to a subject.

Pharmaceutical compositions adapted for nasal and pulmonary administration may comprise solid carriers such as powders, which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for transdermal administration may be provided as discrete patches intended to remain in intimate contact with the epidermis of the recipient over a prolonged period of time.

III. Methods of Treatment

The present invention also provides a method of treating a disease or disorder characterized by an unbalanced nucleotide pool in a subject in need thereof comprising administering to the subject a therapeutically effective amount of a composition described herein comprising Form B deoxycytidine.

In some embodiments, the method further comprises administering to the subject a therapeutically effective amount of a second composition comprising deoxythymidine.

In other embodiments, one composition is administered that comprises both deoxycytidine and deoxythymidine.

In one embodiment, a composition comprising Form B deoxycytidine and at least one residual solvent is administered to a subject, wherein the at least one residual solvent is selected from ICH class 2 and class 3 solvents and the concentration of the at least one residual solvent is less than about 10% of the ICH concentration limit for each residual solvent.

In a more particular embodiment, a composition consisting of Form B deoxycytidine and at least one residual solvent is administered to the subject, wherein the at least one residual solvent is selected from ICH class 2 and class 3 solvents and the concentration of the at least one residual solvent is less than about 10% of the ICH concentration limit for the each residual solvent. Any composition, including pharmaceutical compositions, described herein above can be administered.

In a particular embodiment, a composition comprises Form B deoxycytidine and at least one of the following: (a) from 1 ppm to about 300 ppm methanol, (b) from 1 ppm to about 89 ppm toluene, (c) from 1 ppm to about 60 ppm methylene chloride, (d) from 1 ppm to about 500 ppm ethanol, (e) from 1 ppm to about 500 ppm TBME, (f) from 1 ppm to about 500 ppm acetone, (g) from 1 ppm to about 500 ppm ethyl acetate, and (h) from 1 ppm to about 500 ppm n-heptane.

In preferred embodiments, ICH class 1 solvents, in particular 1,2-dichloroethane, are undetectable in the compositions.

In another embodiment, a pharmaceutical composition comprising Form B deoxycytidine, at least one residual solvent and a pharmaceutically acceptable carrier described herein is administered, wherein the residual solvent is selected from ICH class 2 and class 3 solvents and the concentration of the at least one residual solvent is less than about 10% of the ICH concentration limit for each residual solvent.

In a more particular embodiment, a pharmaceutical composition consisting of Form B deoxycytidine, deoxythymidine, at least one residual solvent and at least one pharmaceutically acceptable carrier described herein is administered, wherein the residual solvent is selected from ICH class 2 and class 3 solvents and the concentration of the at least one residual solvent is less than about 10% of the ICH concentration limit for each residual solvent. In a particular embodiment, the pharmaceutical composition is the fixed-dose powder composition described above.

In yet another embodiment, a method of treating a disease or disorder characterized by an unbalanced nucleotide pool in a subject in need thereof comprises administering to the subject a therapeutically effective amount of (1) a first composition comprising Form B deoxycytidine at least one residual solvent, (2) a second composition comprising deoxythymidine and, optionally, at least one residual solvent, wherein the at least one residual solvent is selected from ICH class 2 and class 3 solvents and the concentration of the at least one residual solvent is less than about 10% of the ICH concentration limit for each residual solvent. In such embodiments, the combined residual solvent amounts from (1) and (2) are less than about 10% of the ICH concentration limit for that particular residual solvent.

In a particular embodiment, the first composition (i.e., (1)) and/or second composition (i.e., (2)) is a pharmaceutical composition further comprising at least one pharmaceutically acceptable carrier.

Regardless of whether the deoxycytidine and deoxythymidine are administered in the same or separate pharmaceutical compositions, the ratio of deoxycytidine to deoxythymidine can vary. For example, they can be in a ratio of 50/50, or in ratios of about 5/95, 10/90, 15/85, 20/80, 25/75, 30/70, 35/65, 40/60, 45/55, 55/45, 60/40, 65/35, 70/30, 75/25, 80/20, 85/15, 90/10, and 95/5.

Diseases or disorders characterized by unbalanced nucleotide pools that can be treated by the method of the current invention include, but are not limited to, those characterized by mutations in the following genes: TK2; DGUOK; TYMP; RRM2B; SUCLA2; SUCLG1; and MPV17. In a preferred embodiment, the disorder is a mitochondrial DNA depletion syndrome (MDS). In a more preferred embodiment, the MDS includes disorders of a myopathic form characterized by mutations in TK2, an encephalomyopathic form characterized by mutations in SUCLA2, a neurogastrointestinal encephalopathy form characterized by mutations in TYMP, and a hepatopathic form characterized by mutations in DGUOK, POLG, and MPV17. In a most preferred embodiment, the disorder is a thymidine kinase 2 deficiency, characterized by mutation(s) in the TK2 gene.

Administration of the pharmaceutical compositions should begin as soon as the disorder characterized by unbalanced nucleotide pools, e.g., MDS, is suspected and continue throughout the life of the patient. Test for the diagnosis of such disorders including TK2 deficiency are known in the art.

By way of example, dT and dC are administered in mixture of equal amounts for TK2 deficiency. Selection of a therapeutically effective dose will be determined by the skilled artisan considering several factors, which will be known to one of ordinary skill in the art. Such factors include the particular form of the deoxynucleoside, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

A preferred dose ranges from about 100 mg/kg/day to about 1,000 mg/kg/day. A further preferred dose ranges from about 200 mg/kg/day to about 800 mg/kg day. A further preferred dose ranges from about 250 mg/kg/day to about 400 mg/kg/day. These dosage amounts are of individual deoxynucleosides or of a composition with a mixture of more than one deoxynucleosides, e.g., dT and dC. For example, a dose can comprise 400 mg/kg/day of dT alone. In a further example, a dose can comprise a mixture of 200 mg/kg/day of dT and 200 mg/kg/day of dC. In a further example, a dose can comprise 400 mg/kg/day of a mixture of dT and dC.

Administration of the deoxynucleosides can be once a day, twice a day, three times a day, four times a day, five times a day, up to six times a day, preferably at regular intervals. For example, when the deoxynucleosides are administered four times daily, doses would be at 8:00 AM, 12:00 PM, 4:00 PM, and 8:00 PM.

Doses can also be lowered if being administered intravenously or intrathecally.

Preferred dose ranges for such administration are from about 50 mg/kg/day to about 500 mg/kg/day.

Dosing can be adjusted to optimize the effects in the subject. For example, the deoxynucleosides can be administered at 100 mg/kg/day to start, and then increased over time to 200 mg/kg/day, to 400 mg/kg/day, to 800 mg/kg/day, up to 1000 mg/kg/day, depending upon the subject's response and tolerability.

A subject can be monitored for improvement of their condition prior to increasing the dosage. A subject's response to the therapeutic administration of the deoxynucleosides can be monitored by observing a subject's muscle strength and control, and mobility as well as changes in height and weight. If one or more of these parameters increase after the administration, the treatment can be continued. If one or more of these parameters stays the same or decreases, the dosage of the deoxynucleosides can be increased.

The deoxynucleosides can also be co-administered with other agents. Such agents would include therapeutic agents for treating the symptoms of the particular form of MDS. In particular, for TK2 deficiency, the dT and dC can be co-administered with an inhibitor of ubiquitous nucleoside catabolic enzymes, including but not limited to enzyme inhibitors such as tetrahydrouridine (inhibitor of cytidine deaminase) and immucillin H (inhibitor of purine nucleoside phosphorylase) and tipiracil (inhibitor of thymidine phosphorylase). Such inhibitors are known and used in the treatment of some cancers.

EXAMPLES

Example 1: Preparation of Form B Deoxycytidine

Form B deoxycytidine was produced by the following 130 kg engineering method.

Step 1: The concentrated residue (crude deoxycytidine) of Reactor R-6424 was blocked by vacuum. 924 kg of ethanol (99.5%) was charged through a dedicated pipe by passing the filter housing.

Step 2: The reactant in Reactor R-6426 was stirred for at about 30 minutes.

Step 3: The reactant of Reactor R-6426 was vacuum distilled using not more than 70° C.

Step 4: The concentrated residue of Reactor R-6426 was released using nitrogen. 98 L (0.25 volumes) of purified water was passed through a dedicated pipe by passing the filter housing.

Step 5: The reactant in Reactor R-6426 was stirred for about 10 minutes.

Step 6: The internal temperature of Reactor R-6426 was increased to about 48° C.

Step 7: The internal temperature was maintained and stirred until the mixture dissolved by visual inspection.

Step 8: Reactor R-6425 was under vacuum. 308 kg (0.70 volumes) of ethanol (99.5%) was charged through the dedicated pipe, then released using nitrogen vacuum.

Step 9: The internal temperature of Reactor R-6426 was maintained between 40° C. and 50° C. The pressurized ethanol (99.5%) of Reactor R-6425 was slowly added to Reactor R-6426 with nitrogen in a manner that prevented precipitation of crystals.

Step 10: 616 kg (1.58 volumes) ethanol (99.5%), 702 kg (1.8 volumes) ethyl acetate and 730 kg (1.36 volumes) heptane were charged to Reactor R-6425 under vacuum. The vacuum was released using nitrogen. The mixture was stirred.

Step 11: The internal temperature of R-6426 was maintained between 40° C. and 50° C. The pressurized mixture of Reactor R-6425 was slowly added to Reactor R-6426.

Step 12: The internal temperature of Reactor R-6426 was cooled to between 20° C. and 30° C.

Step 13: The mixture was stirred for 1 hour.

Step 13: The internal temperature of Reactor R-6426 was cooled to between 0° C. and 10° C.

Step 14: The mixture was stirred for about 1 hour.

Step 15: The internal temperature of Reactor R-6426 was maintained between 0° C. and 10° C.

Step 16: The crystals were collected using a centrifugal filter and washed with ethyl acetate. The crystals were characterized as Form B deoxycytidine by XRPD analysis (see Example 2).

Figure 2:
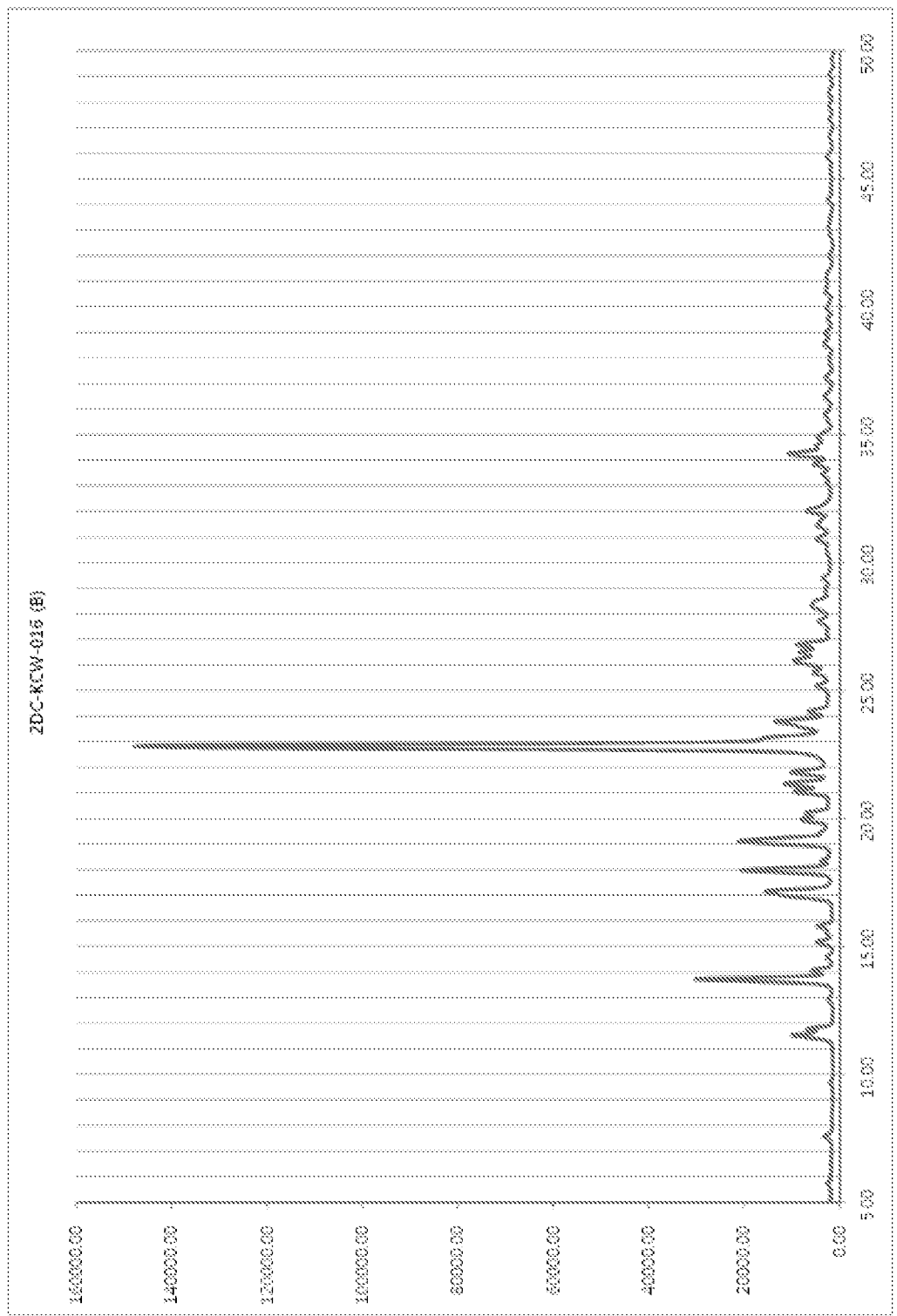
FIG. 2: illustrates the X-ray diffraction pattern of Form B deoxycytidine.

Example 2: Lot Testing Results 4 kg-scale production of dC provided Form B dC (FIG. 2). Scale-up of manufacturing resulted in a mixture of Form A and Form B dC (FIG. 1) and an increase in the residual solvent content of the final API.

Lot 2DC(7)/S-P-17001 was produced at 4 kg scale.

Lots 2DC(7)-6-18001, 2DC(7)-6-18002 and 2DC(7)-6-18003 in Table 1, below, were 55 kg manufacturing lots. These lots were prepared with a different method than described herein in Example 1 and produced a mixture of Forms A and B, as in FIG. 1.

Lots 2DC(7)-E-6-19001 and 2DC(7)-E-6-19002 were 130 kg manufacturing runs that used the process described in Example 1 and provided the Form B polymorph (FIG. 2).

TABLE 1

| Parameter | Specifications | 2DC(7)/S-P-17001 | JDH-2DC(7)-010 | 2DC(7)-6-18001 | 2DC(7)-6-18002 | 2DC(7)-6-18003 | 2DC(7)/E-6-19001 | 2DC(7)E-6-19002 |
|---|---|---|---|---|---|---|---|---|
| Appearance | White to off-white powder | Conform | White Powder | Conform | Conform | Conform | Conform | Conform |
| ID by IR | Conforms, to the reference standard | Conform | Conform | Conform | Conform | Conform | Conform | Conform |
| ID by HPLC | Conforms to the reference standard | Conform | Conform | Conform | Conform | Conform | Conform | Conform |
| Assay by HPLC | 98.0-102.0% | 99.0% | 100.1% | 99.1% | 99.8% | 99.7% | 100.0% | 98.6% |
| Purity and Related Substances by HPLC | Purity NLT 99.0% | 99.9% | 100.0% | 100.0% | 100.0% | 100.0% | 100.0% | 100.0% |
| | Cytosine NMT 0.5% | 0.0% | ND | 0.0% | ND | ND | ND | ND |
| | Total Impurities NMT 1.0% | 0.1% | ND | 0.0% | 0.0% | 0.0% | 0.0% | 0.0% |
| Water Content | NMT 0.5% | 0.1% | 0.0% | 0.0% | 0.1% | 0.1% | 0.1% | 0.1% |
| Specific Optical Rotation | +57.0° C. to +60.0° C. | +58.4° | +59.0° | +58.4° | +59.4° | +58.6° | +58.7° | +58.2° |
| Residual Solvents | <3000 ppm Methanol | ND | ND | ND | ND | ND | ND | ND |
| | <890 ppm Toluene | ND | ND | ND | ND | ND | ND | ND |
| | <600 ppm Dichloromethane | ND | ND | ND | ND | ND | ND | ND |
| | <5000 ppm tert-butyl methyl ether | ND | ND | ND | ND | ND | ND | ND |
| | <5000 ppm ethyl acetate | ND | ND | ND | ND | ND | 64 ppm | ND |
| | <5000 ppm n-Heptane | 62 ppm | 46 ppm | 91 ppm | 80 ppm | 94 ppm | 29 ppm | 25 ppm |
| | <5000 ppm Ethanol | 494 ppm | 132 ppm | 272 ppm | 749 ppm | 559 ppm | 176 ppm | ND |
| | <5 ppm 1,2-Dichloroethane | ND | ND | ND | ND | ND | ND | ND |
| Residue on Ignition | NMT 0.5% | 0.3% | 0.3% | 0.3% | 0.3% | 0.3% | 0.0% | 0.0% |

XRPD data for a mixture of A and B dC isoforms (2DC (A+B mix)), the B isoform produced in the small-scale manufacturing run (2DC(7)/S-P-17001 initial) and the isolated A isoform is provided in Table 2. The stability Form B was confirmed by determining the XRPD after 12 months of storage (2DC(7)/S-P-17001 12 month).

TABLE 2

| XRPD Spectrum (2-Theta) | | | |
|---|---|---|---|
| 2DC (A + B mix) | 2DC(7)/S-P-17001 initial | 2DC(7)/S-P-17001 12 month | 2DC (A) |
| 8.4 | ND | ND | 8.4 |
| 11.6 | 11.5 | 11.5 | ND |
| 11.8 | 11.8 | 11.8 | ND |
| 13.0 | ND | ND | 12.9 |
| 13.8 | 13.7 | 13.7 | ND |
| 14.2 | ND | ND | 14.2 |
| 15.7 | ND | ND | ND |
| 17.0 | ND | ND | 16.8 |
| 17.2 | 17.2 | 17.2 | ND |
| 18.0 | 18.0 | 18.0 | ND |
| 18.5 | ND | ND | 18.4 |
| 19.2 (trace) | 19.2 | 19.2 | ND |
| 19.4 | ND | ND | 19.4 |
| 20.0 | 20.2 | 20.2 | ND |
| 21.4 | 21.1 | 21.1 | 21.3 |
| 21.8 | 21.4 | 21.4 | 21.6 |
| 22.2 | 21.8 | 21.8 | 22.2 |
| 23.0 | 22.8 | 22.8 | ND |
| 28.4 | ND | ND | 28.4 |
| 30.0 | ND | ND | 30.0 |
| 30.6 | ND | ND | 30.6 |

Example 3: Residual Solvent Content of Commercial Materials

Samples of dC and dT purchased from a commercial supplier (Carbosynth) were analyzed by GS-MS to determine residual solvent content. The results are provided in the Table below:

| Solvent | ICH limit | dT (batch 1) | dT (batch 2) | dC (batch 1) | dC (batch 2) |
|---|---|---|---|---|---|
| Methanol | 3,000 ppm | 163 | 179 | 386 | 397 |
| Toluene | 890 ppm | ND | ND | 8 | ND |
| Methylene Chloride | 600 ppm | ND | ND | ND | ND |
| tBME | 5,000 ppm | ND | ND | ND | ND |
| Acetone | 5,000 ppm | ND | ND | ND | ND |
| Ethyl Acetate | 5,000 ppm | ND | ND | ND | ND |
| n-Heptane | 5,000 ppm | ND | ND | ND | ND |
| Ethanol | 5,000 ppm | ND | ND | ND | ND |
| 1,2-DCE | 5 ppm | ND | ND | ND | ND |

Example 4: Form B Deoxycytidine Stability Study

A study was conducted to determine the stability of Form B deoxycytidine prepared by the methods in Example 1 over a 12-month period. Four lots of material were studied: (1) and (2) were packaged in a polyethylene (PE) bag sealed with a cable tie, (3) was packed in a PE bag with silica gel sealed with a cable tie, and (4) was packaged in a PE drum sealed with a cap.

The following test attributes were measured:
Appearance (white to off-white powder)
IR trace
HPLC
    Not less than 99.0% pure
    Not more than 1.0% total impurities
    Not more than 0.5% cytosine
    Less than 0.05% a-anomer
Water content
    Not more than 0.5%
Specific Rotation (+57.0° to +60.0)°
Residue on Ignition
    Not more than 0.5%
Residual Solvents (GC)
    MeOH: Not more than 3,000 ppm
    Toluene: Not more than 890 ppm
    Methylene chloride: Not more than 600 ppm
    MTBE: Not more than 5,000 ppm
    Ethyl acetate: Not more than 5,000 ppm
    n-heptane: Not more than 5,000 ppm
    Ethanol: Not more than 5,000 ppm
Elemental impurities
    Cd: Not more than 5 ppm
    Pb: Not more than 5 ppm
    As: Not more than 15 ppm
    Hg: Not more than 30 ppm
    Co: Not more than 50 ppm
    V: Not more than 100 ppm
    Ni: Not more than 200 ppm
    Ti: Not more than 8 ppm
    Au: Not more than 100 ppm
    Pd: Not more than 100 ppm
    Ir: Not more than 100 ppm
    Os: Not more than 100 ppm
    Rh: Not more than 100 ppm
    Ru: Not more than 100 ppm
    Se: Not more than 150 ppm
    Ag: Not more than 150 ppm
    Pt: Not more than 100 ppm
    Mo: Not more than 3,000 ppm
    Cu: Not more than 3,000 ppm
    Cr: Not more than 11,000 ppm
Microbial Content
    Total Aerobic Microbial count: Not more than 100 CFU/g
    Total Combined Yeasts and Molds Count: Not more than 100 CFU/g Two sets of conditions were applied: (1) long-term storage (25±2° C./60±5% relative humidity) and (2) accelerated storage (40±2° C./75±5% relative humidity)

All attributes were measured initially (0 months) to confirm compliance with the standards above. Appearance, IR, HPLC and water content were then measured at 3, 6, 9 and 12 months to confirm compliance. Microbial content was measured again at 12 months. There were no significant changes observed from initial to 12 months across all test attributes measured.

Example 5: Fixed-Dose Pharmaceutical Composition

A fixed-dose powder for oral solution containing 2'-Deoxycytidine (2.0 g) and 2'-Deoxythymidine (2.0 g) was prepared with the amounts provided in the table below. The powder for oral solution was packed in foil pouch (stick pack) constructed of laminated polyethylene terephthalate, aluminum and low-density polyethylene. The oral solution was prepared by dissolving the powder containing in water before administration to the patients.

TABLE 1

| Composition of Powder for Oral Solution | | | |
|---|---|---|---|
| Name of Ingredient | Function | Quantity (mg per stick pack) | Percentage composition |
| 2'-Deoxycytidine | Drug substance | 2000.00 | 48.25 |
| 2'-Deoxythymidine | Drug substance | 2000.00 | 48.25 |
| Silica Colloidal Anhydrous (Aerosil 200) | Glidant | 124.352 | 3.00 |
| Magnesium Stearate | Lubricant | 20.725 | 0.50 |
| Total: | | 4145.08 | 100.0 |

What is claimed is:

1. A composition comprising Form B deoxycytidine and at least one residual solvent, wherein
Form B deoxycytidine is characterized by a powder X-ray diffraction (XRPD) pattern comprising peaks at 13.7, 17.2, 18.0, 19.2 and 22.8 degrees 2θ (±0.2 degrees 2θ), and
the at least one residual solvent is selected from the group consisting of methanol, toluene, methylene chloride, ethanol, tert-butylmethyl ether, acetone, ethyl acetate, and n-heptane, and the concentration of the at least one residual solvent is less than about 10% of the ICH concentration limit for each residual solvent;
wherein the composition is stable for at least 3 months at 25±2° C. and 60±5% relative humidity.

2. The composition of claim 1, wherein the Form B deoxycytidine further comprises one or more of the following XRPD peaks: 11.5, 11.8, 20.2, 21.1, 21.4 and 21.8 degrees 2θ (±0.2 degrees 2θ).

3. The composition of claim 1, comprising less than about 100 ppm ethyl acetate, less than about 100 ppm n-heptane and less than about 200 ppm ethanol.

4. The composition of claim 1, comprising less than about 70 ppm ethyl acetate, less than about 50 ppm n-heptane and less than about 200 ppm ethanol.

5. The composition of claim 1, wherein composition comprises at least one of the following: (a) from 1 ppm to about 300 ppm methanol, (b) from 1 ppm to about 89 ppm toluene, (c) from 1 ppm to about 60 ppm methylene chloride (d) from 1 ppm to about 500 ppm ethanol, (e) from 1 ppm to about 500 ppm TBME, (f) from 1 ppm to about 500 ppm acetone, (g) from 1 ppm to about 500 ppm ethyl acetate, and (h) from 1 ppm to about 500 ppm n-heptane.

6. The composition of claim 1, wherein 1,2-dichloroethane is undetectable.

7. The composition of claim 1, further comprising at least one pharmaceutically acceptable carrier.

8. The composition of claim 1, further comprising deoxythymidine.

9. A fixed-dose pharmaceutical composition comprising Form B deoxycytidine, deoxythymidine, at least one residual solvent and at least one pharmaceutically acceptable carrier, wherein:
   a. the at least one residual solvent is selected from the group consisting of methanol, toluene, methylene chloride, ethanol, tert-butylmethyl ether, acetone, ethyl acetate, and n-heptane, and the concentration of the at least one residual solvent is less than about 10% of the ICH concentration limit for each residual solvent;
   b. the composition is in the form of a powder;
   c. the weight ratio of deoxycytidine and deoxythymidine is 50:50; and
   d. Form B deoxycytidine is characterized by a powder X-ray diffraction (XRPD) pattern comprising peaks at 13.7, 17.2, 18.0, 19.2 and 22.8 degrees 2θ (±0.2 degrees 2θ);
wherein the composition is stable for at least 3 months at 25±2° C. and 60±5% relative humidity.

10. The composition of claim 9, wherein the at least one pharmaceutically acceptable carrier comprises at least one glidant and at least one lubricant.

11. The composition of claim 10, wherein the at least one glidant is present in an amount from about 0.1 wt % to about 10 wt %.

12. The composition of claim 11, wherein the at least one glidant comprises colloidal silicon dioxide.

13. The composition of claim 10, wherein the at least one lubricant is present in an amount from about 0.1 wt % to about 1 wt %.

14. The composition of claim 13, wherein the at least one lubricant comprises magnesium stearate.

15. The composition of claim 10, wherein deoxycytidine is present in an amount from about 40 wt % to about 50 wt %.

16. The composition of claim 10, wherein the powder is packaged in a pouch.

17. A method for preparing substantially pure Form B deoxycytidine comprising:
   a. providing crude deoxycytidine comprising a mixture of Form A and Form B polymorphic forms;
   b. contacting the crude deoxycytidine with ethanol to provide a first mixture;
   c. distilling ethanol from the first mixture to provide a residue;
   d. contacting the residue with purified water to provide a second mixture;
   e. heating the internal temperature of the second mixture to an internal temperature of at least about 40° C.;
   f. adding ethanol, ethyl acetate and heptane to the second mixture to provide a third mixture;
   g. cooling the third mixture to provide substantially pure Form B deoxycytidine crystals; and
   h. separating the substantially pure Form B crystals from the third mixture.

18. The method of claim 17, wherein in (f) a first portion of ethanol is added to the second mixture following by a solution comprising a second portion of ethanol, ethyl acetate and n-heptane.

19. The method of claim 17, wherein the third mixture in (g) is cooled to an internal temperature from about 0° C. to about 10° C.

20. A method for treating TK2 deficiency in a subject in need thereof comprising administering to the subject a therapeutically effective amount of a composition comprising Form B deoxycytidine and at least one residual solvent selected from the group consisting of methanol, toluene, methylene chloride, ethanol, tert-butylmethyl ether, acetone, ethyl acetate, and n-heptane, wherein the concentration of the at least one residual solvent is less than about 10% of the ICH concentration limit for each residual solvent;
   wherein Form B deoxycytidine is characterized by a powder X-ray diffraction (XRPD) pattern comprising peaks at 13.7, 17.2, 18.0, 19.2 and 22.8 degrees 2θ (±0.2 degrees 2θ); and
   wherein the composition is stable for at least 3 months at 25±2° C. and 60±5% relative humidity.

21. The method of claim 20, further comprising treating the subject with a therapeutically effective amount of a second composition comprising deoxythymidine.

22. The method of claim 21, wherein the ratio of deoxycytidine to deoxythymidine is about 50/50.

23. The method of claim 21, wherein the second composition is administered to the subject in a daily dose of between about 100 mg/kg/day and about 1,000 mg/kg/day.

24. The method of claim 20, wherein the composition is administered to the subject in a daily dose of between about 100 mg/kg/day and about 1,000 mg/kg/day.

25. A method for treating TK2 deficiency in a subject in need thereof comprising
   (a) dissolving a fixed-dose powder composition in water to provide a solution, wherein the powder composition comprises Form B deoxycytidine, deoxythymidine, at least one residual solvent and at least one pharmaceutically acceptable carrier, wherein
      the at least one residual solvent is selected from the group consisting of methanol, toluene, methylene chloride, ethanol, tert-butylmethyl ether, acetone, ethyl acetate, and n-heptane, and the concentration of the at least one residual solvent is less than about 10% of the ICH concentration limit for each residual solvent; and
      wherein the ratio of deoxycytidine to deoxythymidine is about 50/50; and
   (b) administering the solution to a subject in need thereof;
   wherein Form B deoxycytidine is characterized by a powder X-ray diffraction (XRPD) pattern comprising peaks at 13.7, 17.2, 18.0, 19.2 and 22.8 degrees 2θ (±0.2 degrees 2θ);
   wherein the composition is stable for at least 3 months at 25±2° C. and 60±5% relative humidity.

26. The method of claim 25, wherein the composition comprises from about 1,000 mg to about 5,000 mg of each of Form B deoxycytidine and deoxythymidine.

27. The method of claim 26, wherein the composition comprises about 2,000 mg of each of Form B deoxycytidine and deoxythymidine.

* * * * *